United States Patent [19]
Barwick, Jr. et al.

[11] Patent Number: 5,591,127
[45] Date of Patent: Jan. 7, 1997

[54] PHACOEMULSIFICATION METHOD AND APPARATUS

[76] Inventors: Billie J. Barwick, Jr., 85 Hull St., Beverly, Mass. 01915; James H. Little, 6601 S. Country Club Dr., Oklahoma City, Okla. 73159

[21] Appl. No.: 188,188

[22] Filed: Jan. 28, 1994

[51] Int. Cl.$^6$ ........................................... A61M 1/00
[52] U.S. Cl. ........................................................ 604/66
[58] Field of Search ................. 128/DIG. 13; 604/22, 604/26–28, 30, 31, 35, 65, 67, 73, 120, 121, 66; 607/97; 601/2

[56] References Cited

U.S. PATENT DOCUMENTS

| | | | |
|---|---|---|---|
| 3,812,855 | 5/1994 | Banko | 128/276 |
| 4,168,707 | 9/1979 | Douvas et al. | 128/276 |
| 4,425,116 | 1/1984 | Bilstad et al. | 604/34 |
| 4,457,757 | 7/1984 | Molteno | 604/294 |
| 4,475,904 | 10/1984 | Wang | 604/119 |
| 4,479,761 | 10/1984 | Bilstad et al. | 417/395 |
| 4,521,210 | 6/1985 | Wong | 604/8 |
| 4,627,833 | 12/1986 | Cook | 604/34 |
| 4,713,051 | 12/1987 | Stedde et al. | 604/33 |
| 4,735,610 | 4/1988 | Akkas et al. | 604/119 |
| 4,758,238 | 7/1988 | Sundblom et al. | 604/319 |
| 4,798,580 | 1/1989 | Pemeo et al. | 604/30 |
| 4,904,168 | 2/1990 | Cavoto | 417/477 |
| 4,933,843 | 6/1990 | Scheller et al. | 364/413.01 |
| 4,963,131 | 10/1992 | Wortrich | 604/34 |
| 4,966,131 | 10/1990 | Houghton et al. | 128/24 A |
| 4,983,901 | 1/1991 | Lehmer | 318/685 |
| 5,106,366 | 4/1992 | Steppe | 604/30 |
| 5,154,696 | 10/1992 | Shearing | 604/22 |
| 5,230,614 | 7/1993 | Zanger et al. | 417/477 |
| 5,242,404 | 2/1992 | Conley et al. | 604/65 |
| 5,268,624 | 12/1993 | Zanger | 318/551 |
| 5,324,180 | 6/1994 | Zanger | 417/475 |
| 5,342,293 | 8/1994 | Zanger | 604/22 |

FOREIGN PATENT DOCUMENTS

| | | |
|---|---|---|
| 0085518 | 8/1983 | European Pat. Off. |
| 0293081 | 11/1988 | European Pat. Off. |
| 0359217 | 3/1990 | European Pat. Off. |
| 0362822 | 4/1990 | European Pat. Off. |
| 0555625 | 8/1993 | European Pat. Off. |
| A61F900 | 9/1988 | Germany. |
| 2076476 | 12/1981 | United Kingdom. |
| WO8607249 | 12/1986 | WIPO. |
| 8705793 | 10/1987 | WIPO. |
| WO9106325 | 5/1991 | WIPO. |
| 9211814 | 7/1992 | WIPO. |

*Primary Examiner*—Manuel Mendez
*Attorney, Agent, or Firm*—Walter A. Hackler

[57] ABSTRACT

A method and apparatus for phacoemulsification in which handpiece occlusion is sensed by a vacuum rise beyond a programmable level. The speed of a variable speed peristaltic pump is varied in response to the sensed handpiece occlusion condition. Ultrasonic phaco power can be adjusted in response to the sensed handpiece occlusion condition. The adjustment of the ultrasonic phaco power can be performed separately or in addition to the variation of peristaltic pump speed. In addition, the ultrasonic pulse duty cycles can be varied in response to preset ultrasonic power levels.

1 Claim, 4 Drawing Sheets

PHACOEMULSIFICATION METHOD AND APPARATUS

BACKGROUND OF THE INVENTION

The present invention relates to phacoemulsification and, more particularly, to a method and apparatus for control of phacoemulsification parameters in response to occluded and unoccluded conditions of a phacoemulsification handpiece.

Phacoemulsification techniques are well known in the field of ophthalmology going back to the late 1960's and the work of Dr. Charles Kelman. A full discussion of phacoemulsification is found in Chapter 11 "The Mechanics of Phacoemulsification; Chapter 12 "The Phacoemulsification Procedure"; Chapter 13, "Cataract Removal by Phacoemulsification" and Chapter 14 "Small Pupil Phacoemulsification Techniques" of *The Surgical Rehabilitation of Vision—An Integrated Approach To Anterior Segment Surgery*, edited by Lee T. Norman, W. Andrew Maxwell and James A. Davidson, Gower Medical Publishing, New York, N.Y., 1992, ISBN 0-397-44693-4. Chapters 11–14 thereof are incorporated herein by reference in their entirety.

Currently available phacoemulsification systems are manufactured and sold by Optical Micro Systems, Inc. of North Andover, Mass. under the trademarks "DIPLOMAT", "DIPLOMAT MMP", "OPSYS" and "OPSYS MMP". These systems have control units that include a variable speed peristaltic pump, a vacuum sensor, an adjustable source of ultrasonic power and a programmable microprocessor with operator selected presets for controlling aspiration rate, vacuum and ultrasonic power levels.

It is an object of the present invention to provide control over aspiration rates as a function of the occluded-unoccluded condition of the phacoemulsification handpiece.

It is another object of the present invention to provide control over ultrasonic power levels as a function of the occluded-unoccluded condition of the phacoemulsification handpiece.

It is a further object of the invention to provide variable pulse duty cycles for the ultrasonic power of a phacoemulsification system.

BRIEF DESCRIPTION OF THE INVENTION

A method and apparatus for phacoemulsification in which phacoemulsification parameters are controlled in response to selected conditions. Occlusion of the phacoemulsification handpiece is sensed by a vacuum sensor that provides an input to a computer that varies the speed of a peristaltic pump in response to the sensed vacuum condition. Ultrasonic phaco power levels can be adjusted in addition to or in place of the variations in pump speed in response to the sensed vacuum condition. Ultrasonic phaco pulse duty cycles can be varied in response to preset ultrasonic power levels.

BRIEF DESCRIPTION OF THE DRAWINGS

The objects and features of the invention will best be understood from a detailed description of a preferred embodiment, selected for purposes of illustration and shown in the accompanying drawings, in which.

DETAILED DESCRIPTION OF THE INVENTION

Figure 1:
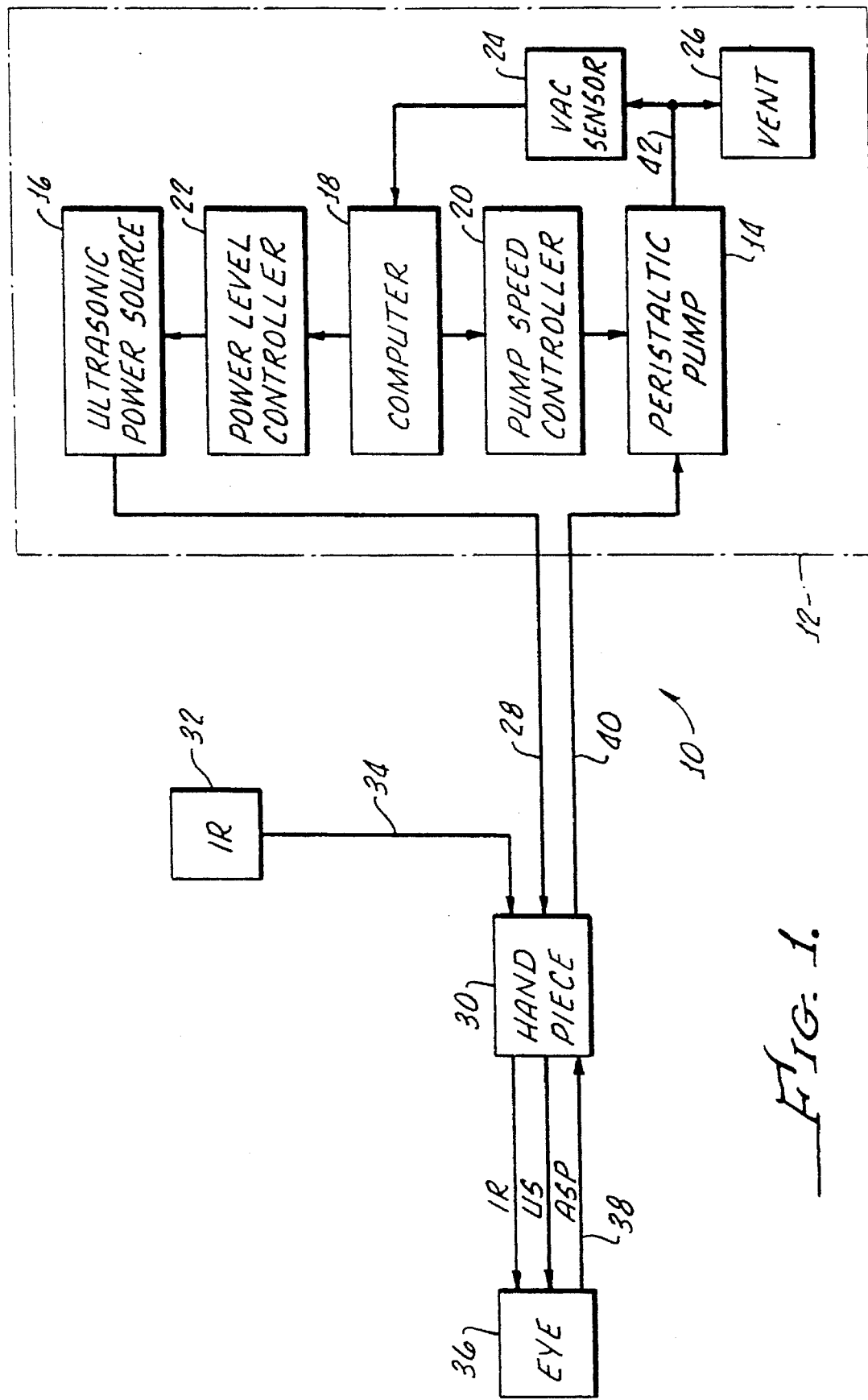
FIG. 1 is a functional block diagram of a phacoemulsification system.

Turning now to the drawings, and particularly to FIG. 1 thereof, there is shown in functional block diagram form a phacoemulsification system indicated generally by the reference numeral 10. The system has a control unit 12, indicated by the dashed lines in FIG. 1 which includes a variable speed peristaltic pump 14, a source of pulsed ultrasonic power 16 and a microprocessor computer 18 that provides control outputs to pump speed controller 20 and ultrasonic power level controller 22. A vacuum sensor 24 provides an input to computer 18 representing the vacuum level on the output side of peristaltic pump 14. Suitable venting is provided by vent 26.

The control unit 12 supplies ultrasonic power on line 28 to a phacoemulsification handpiece 30. An irrigation fluid source 32 is fluidly coupled to handpiece 30 through line 34. The irrigation fluid and ultrasonic power are applied by handpiece 30 to a patient's eye which is indicated diagrammatically by block 36. Aspiration of the eye 36 is achieved by means of the control unit peristaltic pump 14 through lines 38 and 40.

The computer 18 responds to preset vacuum levels in output line 42 from peristaltic pump 14 by means of signals from the previously mentioned vacuum sensor 24. Operation of the control unit in response to the occluded-unoccluded condition of handpiece 30 is shown in the flow diagram of FIG. 2.

Figure 2:
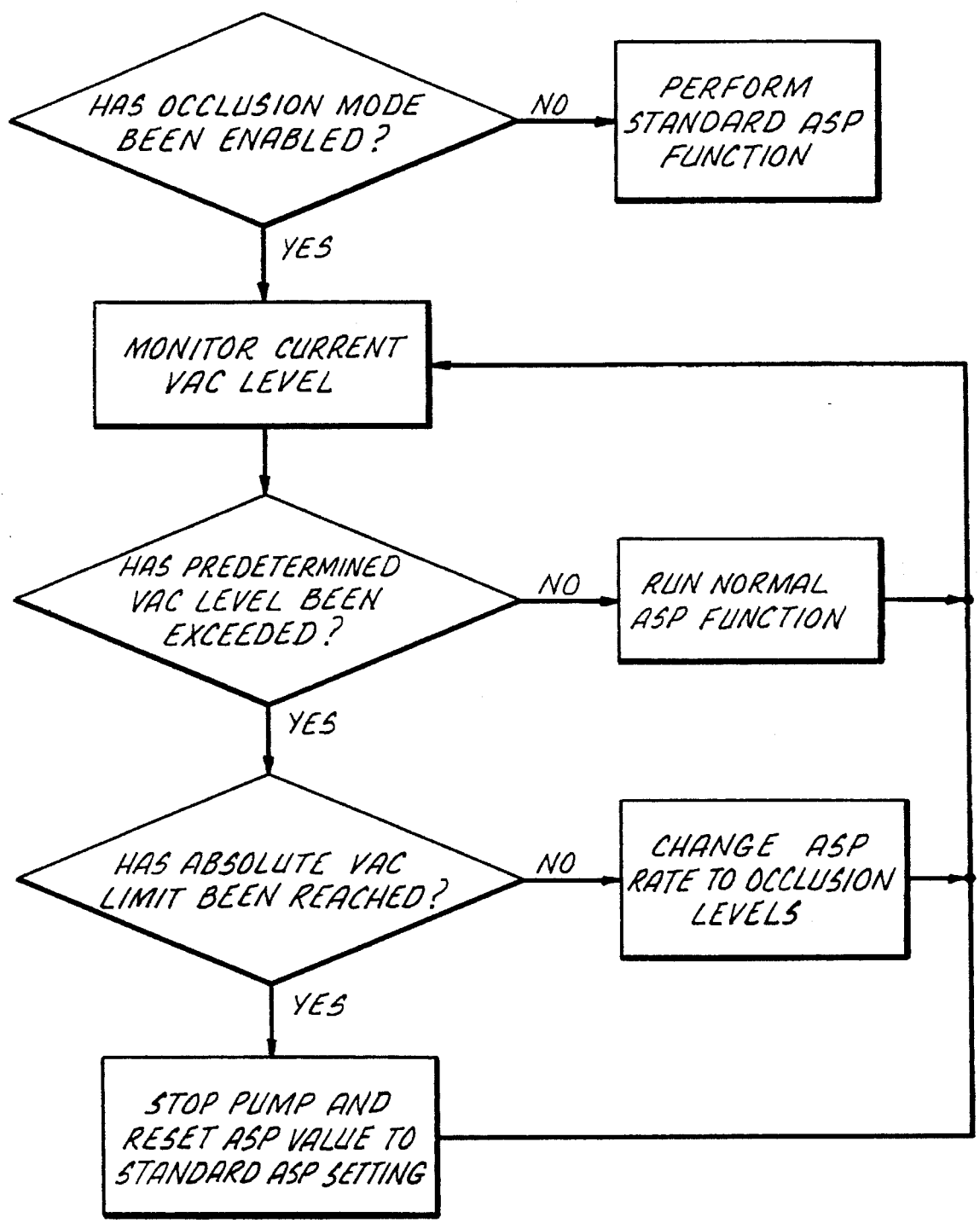
FIG. 2 is a flow chart illustrating the operation of the occluded-unoccluded mode of the phacoemulsification system with variable aspiration rates.

Referring to FIG. 2, if the handpiece aspiration line 38 is occluded, the vacuum level sensed by vacuum sensor 24 will increase. The computer 18 has operator settable limits for aspiration rates, vacuum levels and ultrasonic power levels. As shown in FIG. 2, when the vacuum level sensed by vacuum sensor 24 reaches a predetermined level as a result of occlusion of the handpiece aspiration line 38, computer 18 instructs pump speed controller 20 to change the speed of the peristaltic pump 14 which in turn changes the aspiration rate. It will be appreciated that depending upon the characteristics of the material occluding handpiece 30, the speed of the peristaltic pump 14 can either be increased or decreased. When the occluding material is broken up, the vacuum sensor 24 registers a drop in vacuum level causing computer 18 to change the speed of peristaltic pump 14 to an unoccluded operating speed.

Figure 3:
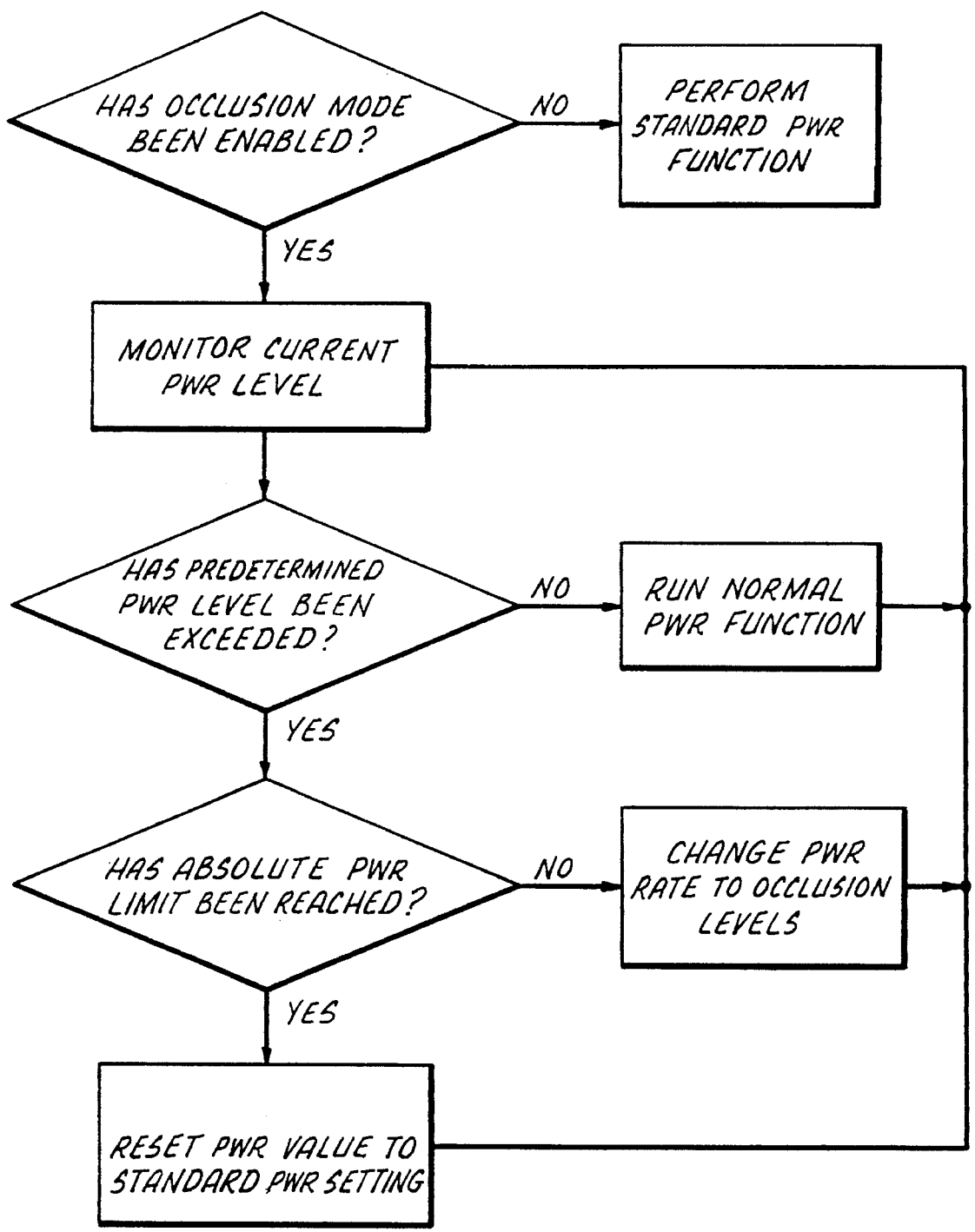
FIG. 3 is a flow chart illustrating the operation of the occluded-unoccluded mode of the phacoemulsification system with variable ultrasonic power levels; and, FIG. 4 is a flow chart illustrating the operation of the variable duty cycle pulse function of the phacoemulsification system.

In addition to changing the phacoemulsification parameter of aspiration rate by varying the speed of the peristaltic pump 14, the power level of the ultrasonic power source 16 can be varied as a function of the occluded or unoccluded condition of handpiece 30. FIG. 3 illustrates in flow diagram form the control of the ultrasonic power source power level by means of computer 18 and power level controller 22. It will be appreciated that the flow diagram of FIG. 3 corresponds to the flow diagram of FIG. 2, but varies the phacoemulsification parameter of the ultrasonic power level.

Figure 4:
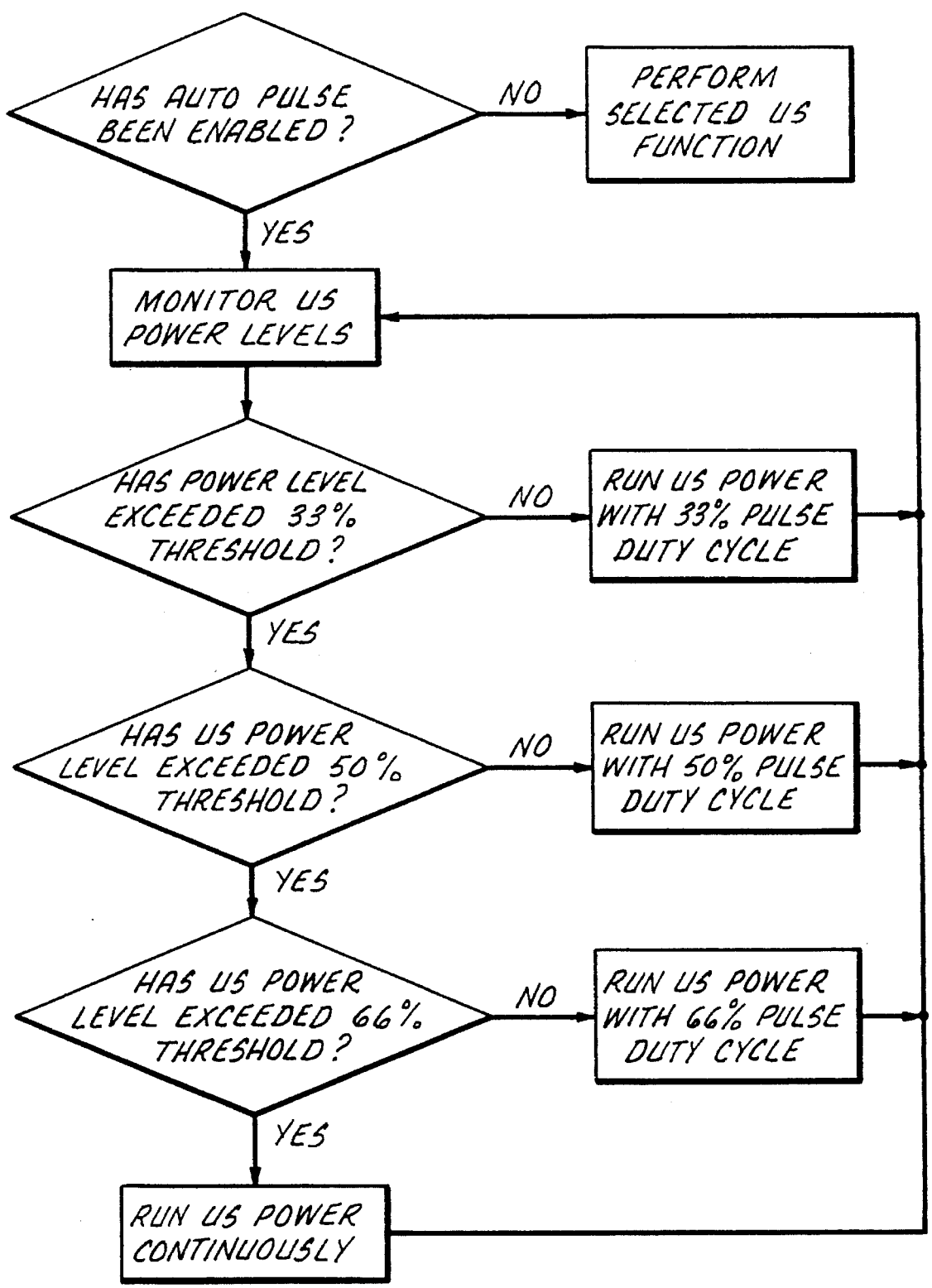

Referring now to FIG. 4, there is shown a flow diagram depicting the control of the ultrasonic power source 16 to produce varying pulse duty cycles as a function of selected power levels. As shown in FIG. 4 and by way of illustration only, a 33% pulse duty cycle is run until the power level exceeds a preset threshold; in this case 33%. At that point, the pulse duty cycle is increased to 50% until the ultrasonic power level exceeds a 50% threshold at which point the pulse duty cycle is increased to 66%. When the ultrasonic power level exceeds 66% threshold, the power source is run continuously, i.e. a 100% duty cycle. Although the percentages of 33, 50 and 66 have been illustrated in FIG. 4, it should be understood that other percent levels can be selected to define different duty cycle shift points.

Having described in detail a preferred embodiment of our invention, it will now be apparent to those having ordinary skill in the art that numerous modifications can be made therein without departing from the scope of the invention as defined in the following claims.

What we claim is:

1. A method of operating a phacoemulsification apparatus having a source of pulsed ultrasonic power, said method comprising the steps of:

(a) running the source of pulsed ultrasonic power at a first pulse duty cycle until a first predetermined power level is exceeded;

(b) then running the source of pulsed ultrasonic power at a second and greater pulse duty cycle until a second and greater predetermined power level is exceeded;

(c) then running the source of pulsed ultrasonic power at a third and still greater pulse duty cycle until a third and still greater predetermined power level is exceeded; and, (d) thereafter running the source of pulsed ultrasonic power at a pulse duty cycle greater than said third pulse duty cycle.

* * * * *